(12) United States Patent
Matsui et al.

(10) Patent No.: US 8,743,357 B2
(45) Date of Patent: Jun. 3, 2014

(54) LIGHT SOURCE DEVICE, SURFACE INSPECTING APPARATUS USING THE DEVICE, AND METHOD FOR CALIBRATING SURFACE INSPECTING APPARATUS USING THE DEVICE

(75) Inventors: Shigeru Matsui, Hitachinaka (JP); Mizuki Oku, Hitachinaka (JP)

(73) Assignee: Hitachi High-Technologies Corporation, Tokyo (JP)

(*) Notice: Subject to any disclaimer, the term of this patent is extended or adjusted under 35 U.S.C. 154(b) by 508 days.

(21) Appl. No.: 13/058,081

(22) PCT Filed: Jul. 15, 2009

(86) PCT No.: PCT/JP2009/063141
§ 371 (c)(1),
(2), (4) Date: Feb. 8, 2011

(87) PCT Pub. No.: WO2010/016386
PCT Pub. Date: Feb. 11, 2010

(65) Prior Publication Data
US 2011/0134418 A1 Jun. 9, 2011

(30) Foreign Application Priority Data
Aug. 8, 2008 (JP) ................. 2008-204969

(51) Int. Cl.
*G01N 21/00* (2006.01)
*G02B 27/20* (2006.01)

(52) U.S. Cl.
USPC ....................... 356/237.5; 362/259

(58) Field of Classification Search
USPC ............... 356/237.1–237.5, 239.1, 239.2, 356/239.7–239.8, 229, 341, 394; 250/559.39–559.49; 382/145, 149
See application file for complete search history.

(56) References Cited

U.S. PATENT DOCUMENTS 5,383,018 A * 1/1995 Sadjadi .................. 356/243.4
5,798,829 A 8/1998 Vaez-Iravani
(Continued)

FOREIGN PATENT DOCUMENTS

JP    11-160245    6/1999
(Continued)

OTHER PUBLICATIONS

Japanese Notification of Reasons for Refusal, w/ partial English translation thereof, issued in Japanese Patent Application No. JP 2012-251769 dated Oct. 29, 2013.

*Primary Examiner* — Gregory J Toatley
*Assistant Examiner* — Dominic J Bologna
(74) *Attorney, Agent, or Firm* — McDermott Will & Emery LLP

(57) ABSTRACT

A surface inspecting apparatus can inspect a smaller defect by using a PSL of a smaller particle size. However, the particle size of the PSL is restricted. In the conventional surface inspecting apparatus, therefore, no consideration has been taken as to how to inspect the defect of such a small particle size as is not set in the PSL which will be needed in the near future in an inspection of a semiconductor manufacturing step. The invention has a light source device for generating light which simulated at least one of a wavelength, a light intensity, a time-dependent change of the light intensity, and a polarization of light which was scattered, diffracted, or reflected by an inspection object, and the light is inputted to a photodetector of the surface inspecting apparatus. The smaller defect can be inspected.

38 Claims, 12 Drawing Sheets

(56) References Cited

U.S. PATENT DOCUMENTS

| | | | |
|---|---|---|---|
| 6,833,914 B1 * | 12/2004 | Bao et al. | 356/237.5 |
| 7,167,582 B2 * | 1/2007 | Ishikawa | 382/144 |
| 7,884,936 B2 * | 2/2011 | Manassen | 356/401 |
| 2003/0223087 A1 * | 12/2003 | Sasazawa et al. | 356/636 |
| 2004/0207836 A1 * | 10/2004 | Chhibber et al. | 356/237.4 |
| 2004/0252297 A1 * | 12/2004 | Fairley et al. | 356/237.5 |

FOREIGN PATENT DOCUMENTS

| | | |
|---|---|---|
| JP | 2001-141666 | 5/2001 |
| JP | 2001-147203 | 5/2001 |
| JP | 2003-185588 | 7/2003 |
| JP | 2008-020271 A | 1/2008 |
| JP | 2008-58239 | 3/2008 |

* cited by examiner

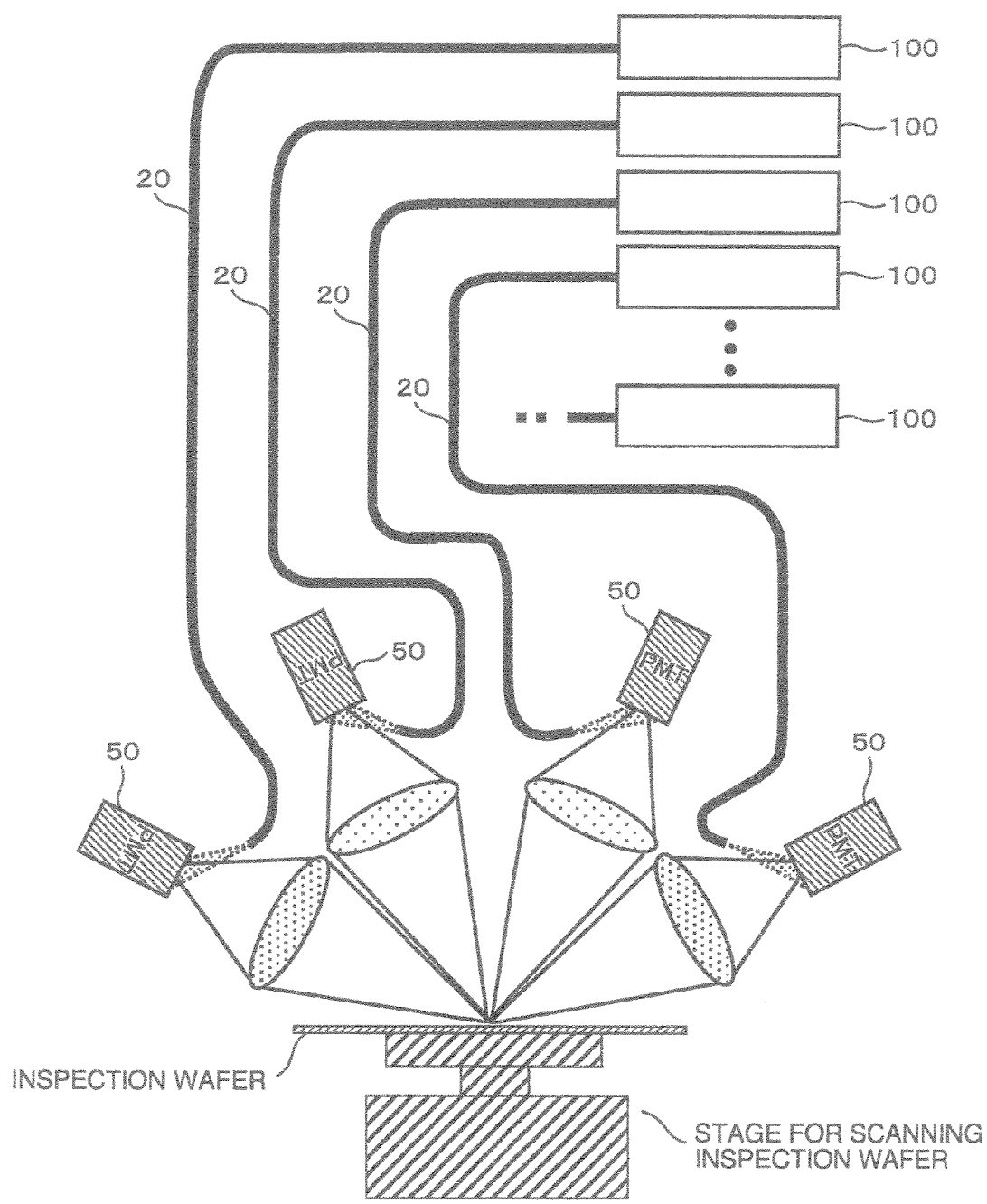

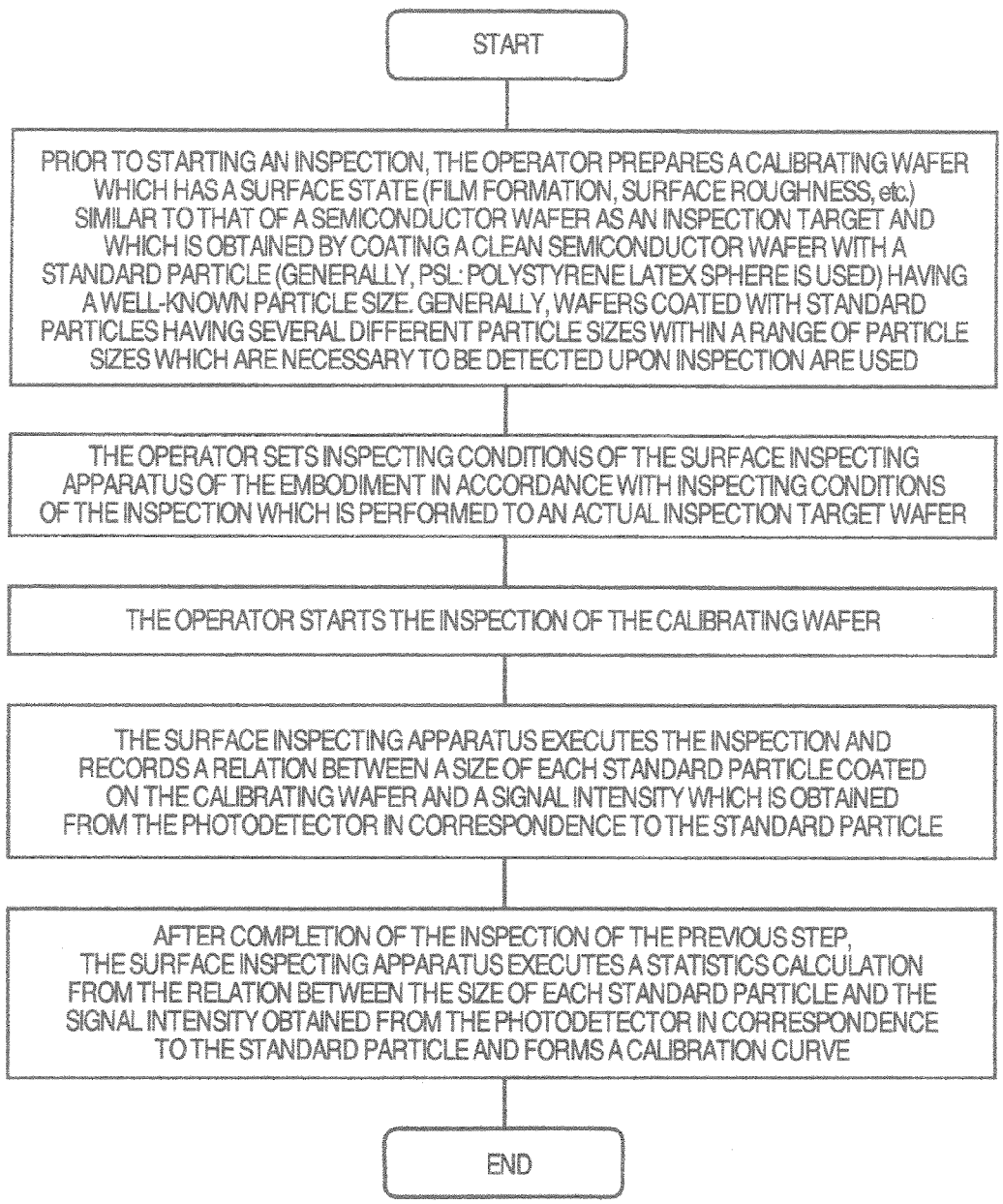

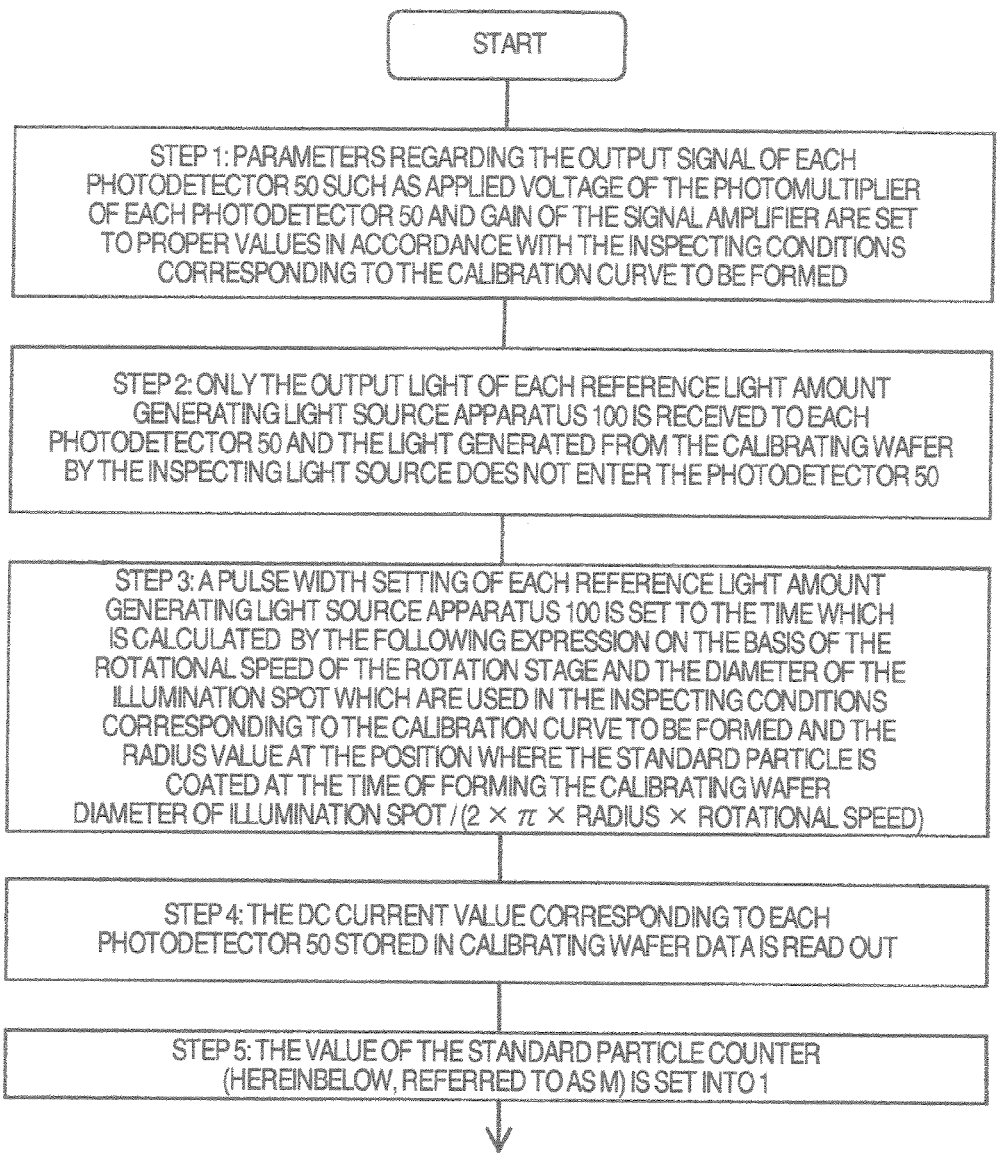

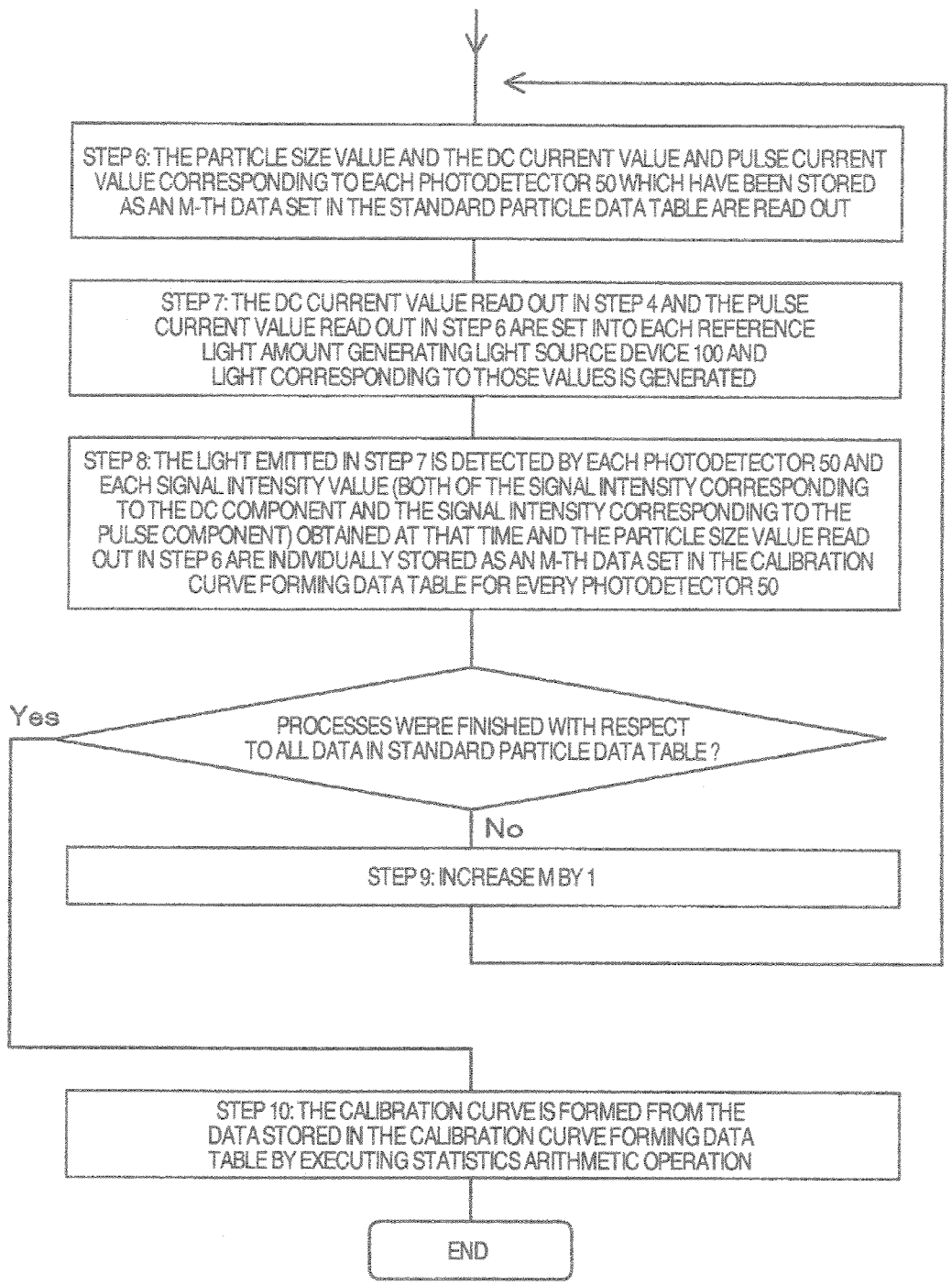

FIG.11

| INSPECTING CONDITIONS (APPARATUS OPERATING CONDITIONS) |
|---|
| 1. ROTATIONAL SPEED OF THE ROTATION STAGE<br>2. ILLUMINATION SPOT DIAMETER<br>3. LASER OUTPUT (THE UNIT IS THE ILLUMINANCE IN THE ILLUMINATION SPOT OR THE TOTAL LIGHT AMOUNT IN THE ILLUMINATION SPOT)<br>4. GAIN SETTING OF EACH PHOTODETECTOR (APPLIED VOLTAGE IN THE CASE OF THE PHOTOMULTIPLIER)<br>5. GAIN SETTING OF THE AMPLIFIER TO AMPLIFY THE OUTPUT SIGNAL OF EACH PHOTODETECTOR |

| CALIBRATING WAFER INFORMATION |
|---|
| 1. ID INFORMATION (FOR EXAMPLE, ROUGHNESS VALUE) REGARDING A MAGNITUDE OF SURFACE ROUGHNESS OF THE WAFER WHICH IS USED<br>2. PARTICLE SIZE RANGE (MIN. VALUE AND MAX. VALUE) OF A PLURALITY OF STANDARD PSL PARTICLES WHICH ARE DEPOSITED<br>3. RADIUS POSITION WHERE THE STANDARD PSL PARTICLE IS DEPOSITED ON THE CALIBRATING WAFER |

FIG.12

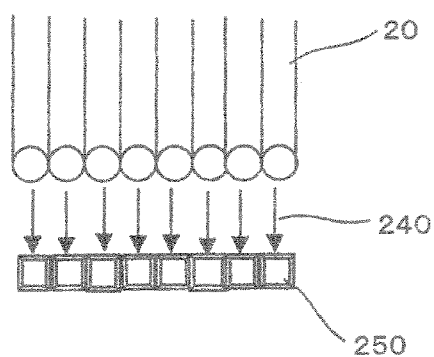

LIGHT SOURCE DEVICE, SURFACE INSPECTING APPARATUS USING THE DEVICE, AND METHOD FOR CALIBRATING SURFACE INSPECTING APPARATUS USING THE DEVICE

RELATED APPLICATIONS

This application is the U.S. National Phase under 35 U.S.C. §371 of International Application No. PCT/JP2009/063141, filed on Jul. 15, 2009, which in turn claims the benefit of Japanese Application No. 2008-204969, filed on Aug. 8, 2008, the disclosures of which Applications are incorporated by reference herein.

TECHNICAL FIELD

The invention relates to a surface inspecting apparatus for inspecting a micro contaminant particle, scratch, dirt, or the like (hereinbelow, they are generally referred to as a defect) existing on the surface of an inspection object (object to be inspected) such as a semiconductor substrate (semiconductor wafer) or the like.

BACKGROUND ART

In a manufacturing line of a semiconductor substrate, a thin film substrate, or the like, in order to monitor a dust generation situation of a manufacturing apparatus, a defect on the surface of the semiconductor substrate, thin film substrate, or the like is inspected.

Hitherto, as a technique for detecting a micro defect on the surface of an inspection object such as a semiconductor substrate or the like, for example, as disclosed in the specification of U.S. Pat. No. 5,798,829, there is such a technique that a collected laser light flux is fixedly irradiated onto the surface of the semiconductor substrate (an illuminated area which is formed onto the surface of the semiconductor substrate by the laser light flux at this time is called an illumination spot) and in the case where a defect exists on the semiconductor substrate, scattered light which is generated from such a defect is detected by a photodetector, thereby inspecting the defects on the whole surface of the semiconductor substrate.

In such a surface inspecting apparatus, generally, an intensity of a signal which is obtained from the photodetector is converted into a size of detected defect and used as an inspection result. Such a conversion is performed in such a manner that a calibrating wafer (wafer for calibration) adhered with a standard particle (generally, PSL: polystyrene latex sphere is used) whose particle size (diameter) has already been known is preliminarily measured before the inspection, a relation between an intensity of scattered light which is generated by the standard particle whose particle size has already been known and the intensity of the signal which is obtained from the photodetector in correspondence to it is previously calculated as a calibration curve, and the actual inspection wafer is inspected, the intensity of the signal which is obtained from the photodetector is applied to the calibration curve and converted into the particle size corresponding to the standard particle. Such a calibrating method has been disclosed in, for example, JP-A-2003-185588 or the like.

CITATION LIST

Patent Literature

Patent Literature 1 JP-A-2003-185588

SUMMARY OF INVENTION

Technical Problem

In the surface inspecting apparatus, by using a PSL of a smaller particle size, the smaller defect can be inspected.

However, the particle size of the PSL is restricted.

Therefore, in the conventional surface inspecting apparatus, no consideration is taken as to how to inspect a defect of such a small particle size that there are no settings in a PSL which will be necessary in the near future in the inspection of a semiconductor manufacturing step.

Solution to Problem

It is one feature of the invention that a surface inspecting apparatus has a light source device for generating light which has simulated at least one of a wavelength, a light intensity, a time-dependent change in light intensity, and a polarization of light which was scattered, diffracted, or reflected by an inspection object, wherein the light is inputted to a photodetector of the surface inspecting apparatus.

It is another feature of the invention that the light extracted from the light source device is constructed by at least an almost direct current (DC) component and an almost pulse component, and at least one of a magnitude of the almost direct current component, a magnitude of the almost pulse component, and a width of the almost pulse component can be changed within an arbitrary range and at an arbitrary resolution.

It is another feature of the invention that the apparatus has a light intensity monitoring detector for receiving a part of the light which is emitted from the light source, wherein a driving power source for the light source can be controlled by using an output signal of the light intensity monitoring detector.

It is another feature of the invention that the apparatus has a light attenuating unit for attenuating the light which is emitted from the light source, wherein the light can be extracted after the light attenuation.

It is another feature of the invention that the light source device has at least one or more optical fibers and the light is extracted from the optical fiber.

It is another feature of the invention that an intensity ratio of the light which is extracted from the plurality of optical fibers can be arbitrarily changed.

It is another feature of the invention that the surface inspecting apparatus has the light source device.

It is another feature of the invention that a relation between the incident light of the photodetector and its output signal intensity is measured by using the light source device, the relation is stored into the surface inspecting apparatus, and when a particle size is calculated by the particle size calculating unit, the stored information is reflected.

It is another feature of the invention that a calibration curve which is used for the particle size calculating unit to convert the output signal of the photodetector into a particle size of a defect is formed by using the light source device.

It is another feature of the invention that a plurality of light source devices are built in the surface inspecting apparatus, the plurality of optical fibers are made to correspond to a plurality of photodetectors, and output ends of the plurality of optical fibers are arranged near the plurality of photodetectors.

Advantageous Effects of Invention

According to the invention, the smaller defect can be inspected.

The invention will be described in more detail hereinbelow by embodiments.

BRIEF DESCRIPTION OF DRAWINGS

FIG. 6 is a diagram for describing a method of inputting output light of the reference light intensity generating light source device to each photodetector of the surface inspecting apparatus in the embodiment 1.

FIG. 7 is a flowchart showing a flow for a conventional calibration curve forming process.

FIG. 10(a) is a flowchart showing a flow for a calibration curve forming process in the embodiment 1.

FIG. 10(b) is a flowchart showing the flow for the calibration curve forming process in the embodiment 1.

FIG. 11 is a table showing input parameters in a GUI at the time of forming the calibration curve in the embodiment 1.

FIG. 12 is an example in the case of inputting the light from the reference light intensity generating light source device to a one-dimensional CCD by using array-shaped optical fibers.

DESCRIPTION OF EMBODIMENTS

Embodiments of the invention will be described hereinbelow by using the drawings.

[Embodiment 1]

Figure 1:
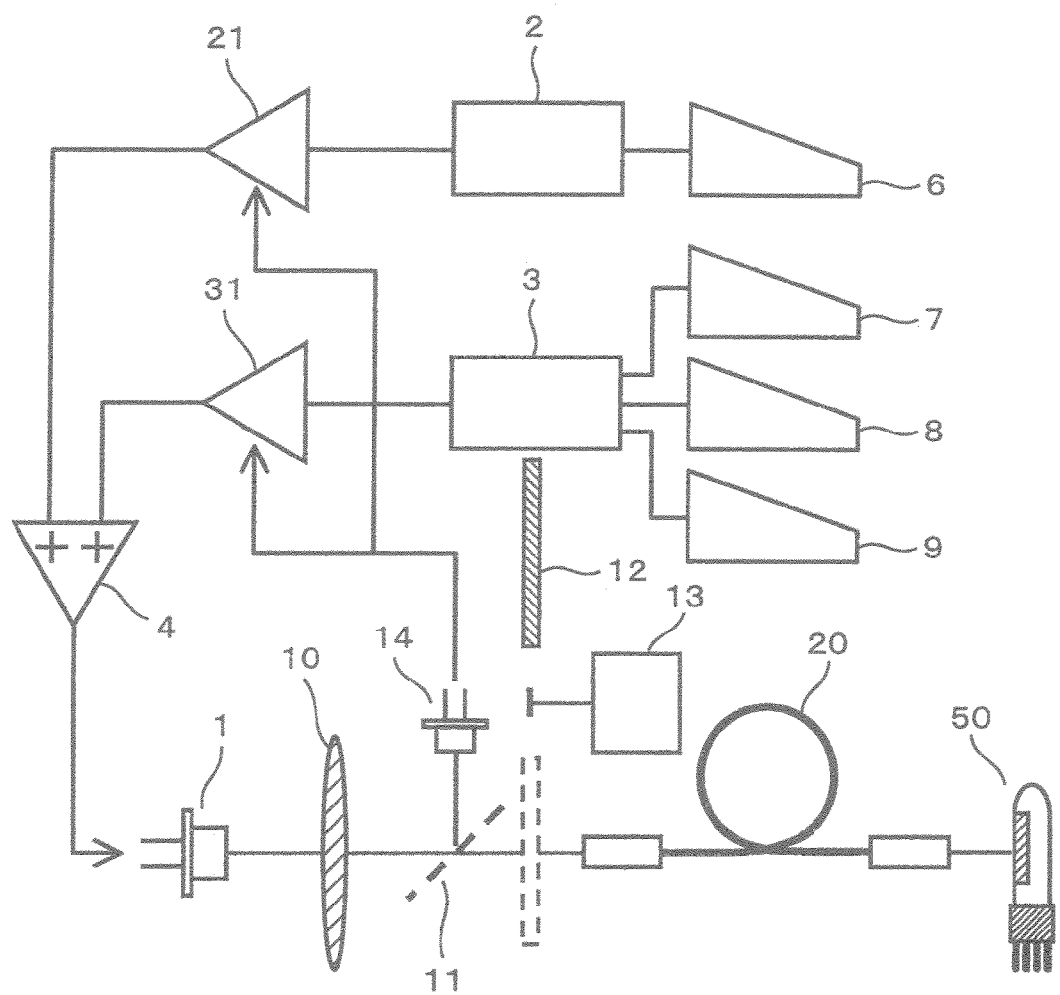
FIG. 1 is a diagram showing a construction of a light source device for generating a reference light intensity according to an embodiment 1.

A first embodiment of a light source device of the invention is shown in FIG. 1.

As a light emitting element 1 serving as a light source, it is desirable to use a small light source of a narrow spectral bandwidth such as light emitting diode, semiconductor laser, diode-pumped solid-state laser, or the like. It is desirable to select a light emitting wavelength of the light emitting element 1 in such a manner that it is almost equal to a wavelength of illumination light which is used by a surface inspecting apparatus which should be simulated and which will be described hereinafter, a light emitting spectral bandwidth of the light emitting element 1 includes the wavelength of the illumination light, or spectral sensitivity characteristics of a photodetector which is used by the surface inspecting apparatus in the case of the wavelength of the illumination light and those in the case of the light emitting wavelength of the light emitting element 1 are almost equal. In the embodiment, since a case where the wavelength of the illumination light of the surface inspecting apparatus which should be simulated and which will be described hereinafter is equal to 355 nm will be explained, an ultraviolet light emitting diode in which a center wavelength of the light emitting spectral bandwidth is equal to 365 nm is used as a light emitting element 1.

Figure 2:
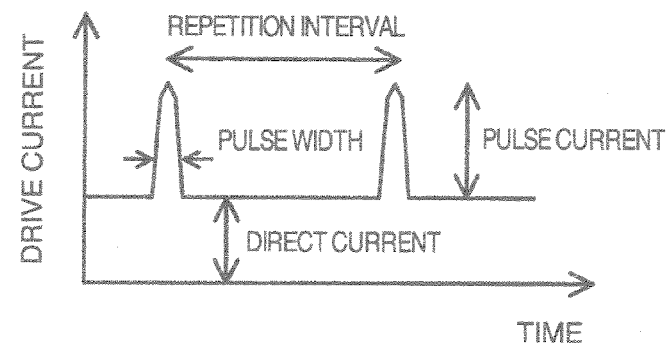
FIG. 2 is a diagram showing a time-dependent change waveform of a light output which is derived from the reference light intensity generating light source device in the embodiment 1.

After a direct current from a direct current generating unit 2 was amplified by a direct current amplifier 21 and after a pulse current from a pulse current generating unit 3 was amplified by a pulse current amplifier 31, both of them are sent to a current adder 4 and added, and an addition current is supplied as a drive current to the light emitting element 1. A direct current setting value input unit 6 is annexed to the direct current generating unit 2. From the input unit 6, the operator can input an amount of DC (direct current) drive current which is supplied to the light emitting element 1. A pulse current setting value input unit 7, a pulse width input unit 8, and a pulse repetition interval input unit 9 are attached to the pulse current generating unit 3. From those input units 7, 8, and 9, the operator can input an amount of pulse drive current which is supplied to the light emitting element 1, its pulse width, and a repetition interval time. A time-dependent change of a light emitting intensity of the light emitting element 1 becomes almost a waveform as shown in FIG. 2. The light emitted from the light emitting element 1 is collected by a condenser lens 10 and enters an incident side end surface of an optical fiber 20.

However, in a state where values of the DC drive current and the pulse drive current which are supplied to the light emitting element 1 are held constant, if an aging deterioration occurs in output characteristics to the applied current of the light emitting element 1, a light intensity which is extracted from the optical fiber 20 in the light source device fluctuates.

To avoid such a fluctuation, in the light source device, a beam splitter 11 is arranged between the condenser lens and the incident side end surface of the optical fiber 20 and a part of the light emitted from the light emitting element 1 is branched by the beam splitter 11 and guided to a detector 14 for monitoring the light intensity. The light intensity monitoring detector 14 is a silicon photodiode and generates an output signal which is proportional to an incident light intensity. This output signal is fed back to the direct current amplifier 21 and the pulse current amplifier 31 and an amplification factor of each amplifier is finely adjusted. That is, when the output signal of the light intensity monitoring detector 14 decreases under such a condition that setting values to the direct current setting value input unit 6 and the pulse current setting value input unit 7 are equal to predetermined values, the amplification factors of the direct current amplifier 21 and the pulse current amplifier 31 are finely adjusted in such a direction as to be increased, and those amplifiers act so that the intensity of the output signal of the light intensity monitoring detector 14 is held constant. Owing to such feedback control, even if the aging deterioration occurred in the light emitting element 1, its influence is suppressed and the light intensity which is extracted from the optical fiber 20 in the light source device can be stabilized so as not to fluctuate.

Further, an ND filter 12 is arranged between the condenser lens and the incident side end surface of the optical fiber 20. The ND filter 12 can be inserted into or removed from an optical path by a switching mechanism 13. Although an amount of light which enters the optical fiber 20 can be reduced by decreasing the drive current of the light emitting element 1, there is a limitation in a lower limit of the drive current which can attenuate the light intensity on the basis of a stable and good linearity. Therefore, if the user wants to reduce the incident light intensity to the optical fiber 20 while exceeding such a range, the ND filter 12 is inserted into the optical path and a light attenuating action by the ND filter 12 and a light attenuating action by the drive current can be combined and used.

A typical specification of measurement light (light to be measured) detected by the built-in photodetector in the general surface inspecting apparatus will now be described. A structure of the general surface inspecting apparatus is as disclosed in, for example, FIG. 6 of JP-A-2008-020271. In an example of the standard inspection conditions of such a surface inspecting apparatus, a rotation stage is rotated at 4000 rotations/minute. A diameter (defined by an outline in which an illuminance decreases to a fraction of a square of a base of a natural logarithm "e" to an illuminance of a center portion of an illumination spot) in the radial direction of a semiconductor wafer of the illumination spot is equal to 10 micrometers. In the case where a contaminant particle has been deposited at a position of a radius of 75 mm on an inspection wafer (wafer to be inspected) (it is assumed here that a size of contaminant particle is sufficiently smaller than 1 micrometer), a time when the contaminant particle passes through the illumination spot of a diameter of 10 micrometers in association with the rotating operation of the rotation stage is equal to $$10/\{2\times\pi\times75\times1000\times(2000/60)\}=3.18\times10^{-7} \quad (s)$$

that is, 318 nanoseconds. Pulse-shaped emitting light having a pulse width of 318 nanoseconds is generated from such a contaminant particle.

In the light source device of the embodiment, by matching setting values in the pulse width input unit with such a value, pulsed light emission having similar time characteristics can be generated. Although an intensity of the pulsed light emission due to a defect depends on a material, a particle size, or the like of the defect, in a region where the particle size of the defect is sufficiently smaller than a wavelength of the illumination light, scattered light of a format called Rayleigh scattering is caused. In a region where the particle size of the defect is larger than such a wavelength and is close to a particle size of about the wavelength, scattered light of a format called Mie scattering is caused. In the Rayleigh scattering region, since the scattered light intensity is proportional to the particle size to the power of six, a small particle size difference appears as a large light intensity difference of the scattered light. For example, if particles range of inspection targets is set from the small particle of 20 nanometers to the large particle of 80 nanometers, a range of the light intensity becomes a dynamic range of about 1000. As mentioned above, in the light source device of the embodiment, since the light emission amount from the light emitting element 1 can be increased or decreased in accordance with a combination of both of the ND filter and the drive current, as compared with the case where the light intensity is increased or decreased only in accordance with the value of the drive current, the present light source device can cope with a light intensity which changes by a large dynamic range without making the light emission amount unstable.

Further, in the surface inspecting apparatus, even when such a defect does not pass through the illumination spot, in the illumination spot, the scattered light (hereinbelow, called "background scattering") is always generated by a micro surface roughness (micro roughness) of the inspection wafer itself (wafer to be inspected). Generally, in the case of a semiconductor wafer subjected to a good polish finishing, such a surface roughness is almost uniform at any position in the semiconductor wafer plane. Therefore, a time-dependent change of an intensity of the background scattering becomes an almost DC component. However, an absolute value of the intensity differs in dependence on a surface finishing state. In the light source device of the embodiment, by changing a value which is inputted to the direct current setting value input unit 6, it is possible to individually match even to such a background scattering showing the different intensity due to the different surface roughness as mentioned above. As mentioned above, in the light source device of the embodiment, by a combination of (1) the setting value into the direct current setting value input unit 6, (2) a setting value into the pulse current setting value input unit 7 and the switching of the ND filter 12, and (3) a setting value into the pulse width input unit 8, in the actual surface inspecting apparatus, when one defect passes through the illumination spot, light similar to measurement light (light to be measured) which enters the photodetector can be generated. Further, in the light source device, by setting the repetition periodic time into (4) a setting value into the pulse repetition interval input unit 9, a single light emission event which is caused from one defect can be repetitively caused at a predetermined time interval.

The light source device of the embodiment can be built in the surface inspecting apparatus and used as a reference light intensity generating apparatus which generates a predetermined amount of light.

Figure 3:
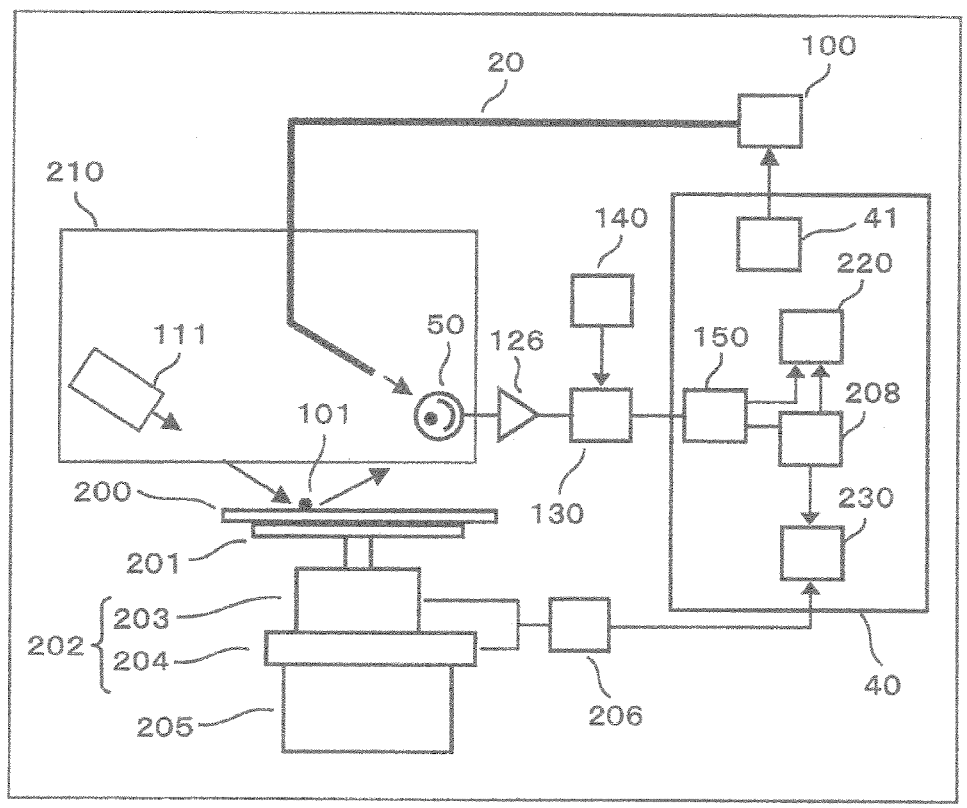
FIG. 3 is a diagram showing a construction of a surface inspecting apparatus in the embodiment 1.

A constructional diagram of the surface inspecting apparatus in which the light source device of the embodiment has been built is shown in FIG. 3. Since the surface inspecting apparatus of FIG. 3 is an apparatus obtained by providing the light source device of the invention into the surface inspecting apparatus shown in FIG. 6 of JP-A-2008-020271 and adding a control function of the light source device thereto, a detailed description of portions other than portions regarding the light source device of the invention and its control is omitted.

Figure 4:
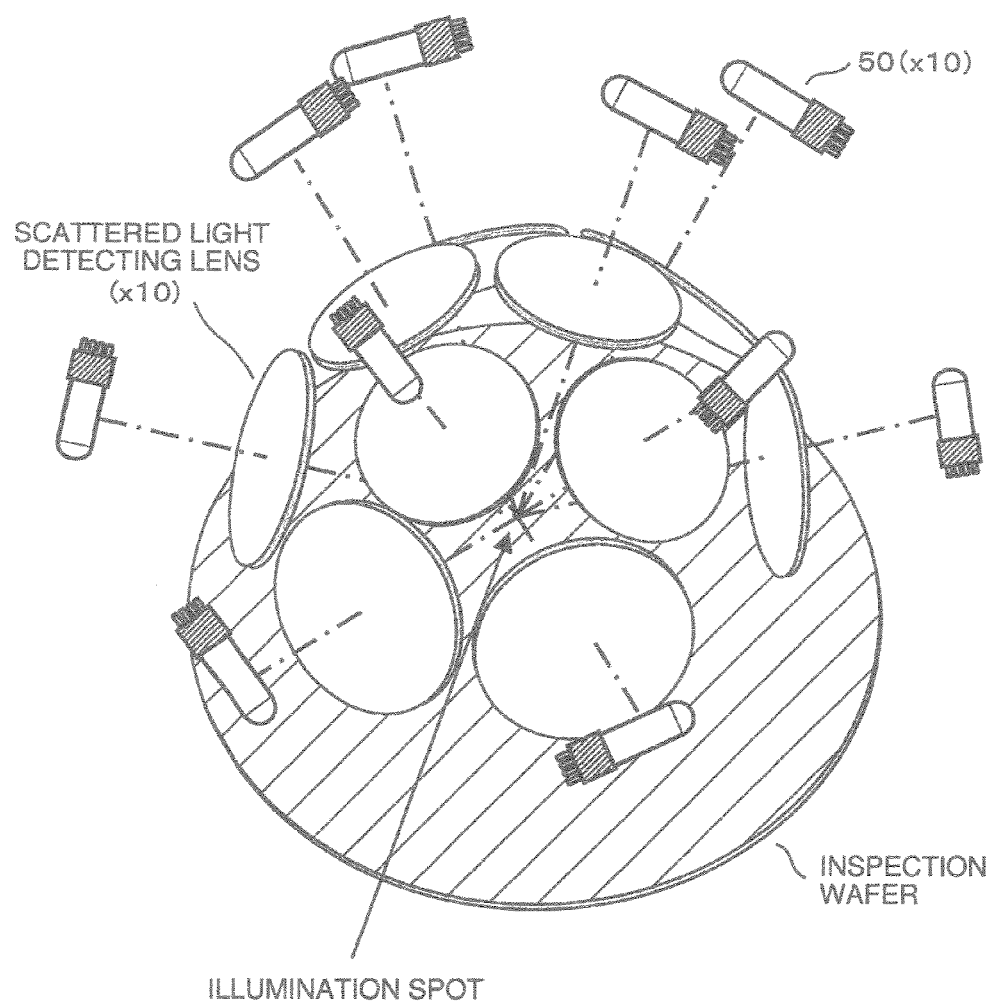
FIG. 4 is a diagram showing a layout of photodetectors of the surface inspecting apparatus in the embodiment 1.

In the surface inspecting apparatus, generally, a plurality of photodetectors are equipped in order to individually capture stereoscopic angular distribution of the scattered light which is generated from the defects on the surface of the inspection object (object to be inspected), that is, components of the scattered light which progresses to different azimuths and elevation angles. In the surface inspecting apparatus of the embodiment, as shown in a bird's-eye view of FIG. 4, ten photodetectors 50 comprising photomultiplier tubes are provided. In the embodiment, ten reference light intensity generating light source devices 100 of the invention are built in the surface inspecting apparatus in correspondence to the number of photodetectors 50. Since each of the above reference light intensity generating light source devices 100 is similar to that described in the first embodiment except for the following points, only different portions will be described in detail.

Figure 5:
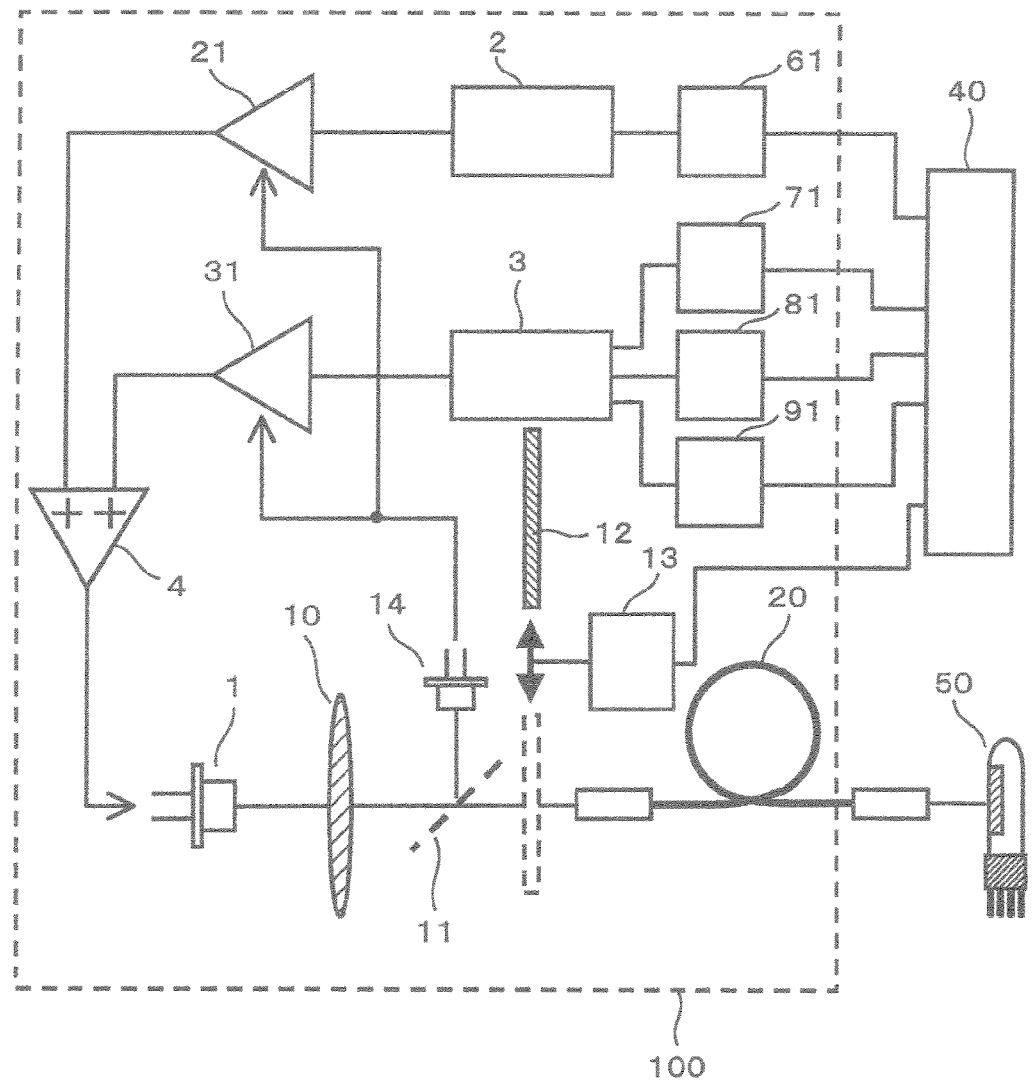
FIG. 5 is a diagram showing a construction of the reference light intensity generating light source device built in the surface inspecting apparatus in the embodiment 1.

(A) As shown in FIG. 5, in place of the direct current setting value input unit 6, pulse current setting value input unit 7, pulse width input unit 8, and pulse repetition interval input unit 9, a direct current setting interface 61, a pulse current setting interface 71, a pulse width setting interface 81, and a pulse generation timing signal interface 91 are attached, respectively, and are connected to a microcomputer 40 for control built in the surface inspecting apparatus. An amount of DC drive current which is supplied to the light emitting element 1, an amount of pulse drive current, its pulse width, and generation timing of the pulse drive current can be controlled by commands from the microcomputer 40 for control.

(B) The switching mechanism 13 inserts or removes the ND filter 12 into/from an optical path by a command from the microcomputer 40 for control.

(C) As shown in a side elevational view of FIG. 6, an outgoing side end surface of the optical fiber 20 is arranged near a photosensing surface of one photodetector 50 corresponding to each reference light intensity generating light source device 100 in such a manner that at the time of the actual inspection of the inspection wafer, it does not obstruct such an operation that the photodetector 50 detects the scattered light which is generated from the defects on the semiconductor wafer, and the light which is extracted from the outgoing side end surface of the optical fiber 20 is effectively irradiated onto the photosensing surface of the photodetector 50.

Hitherto, a calibration curve adapted to convert the output signal from the photodetector into the particle size of the defect upon inspection has been formed by preliminarily executing the following operations prior to performing the actual inspection. FIG. 7 is a flowchart showing a flow for a conventional calibration curve forming process.

Step 1: Before the start of the inspection, the operator prepares a calibrating wafer (wafer for calibration) which has a surface state (film formation, surface roughness, and the like) similar to that of the semiconductor wafer as an inspection target and which is obtained by adhering a clean semiconductor wafer with standard particles (generally, PSL: polystyrene latex spheres are used) whose particle size has been well-known. Ordinarily, the wafers adhered with the standard particles having different particle sizes of a few stages in a range of particle sizes which are necessary to be detected upon inspection are used.

Step 2: The operator sets inspection conditions of the surface inspecting apparatus of the embodiment in accordance with inspection conditions of the inspection which is performed to the actual wafer as an inspection target.

Step 3: The operator starts the inspection of the calibrating wafer.

Step 4: The surface inspecting apparatus executes the inspection and records a relation between a size of each standard particle adhered to the calibrating wafer and the intensity of the signal which is obtained from the photodetector in correspondence to the standard particle.

Step 5: After completion of the inspection of Step 4, the surface inspecting apparatus performs a statistical calculation from the relation recorded in Step 4, that is, the relation between the size of each standard particle and the intensity of the signal obtained from the photodetector in correspondence to the standard particle and forms the calibration curve.

In addition to the conventional function for forming the calibration curve by the calibrating wafer, the surface inspecting apparatus of the embodiment has a function for forming the calibration curve by using the built-in reference light intensity generating light source device 100. Owing to such a function, since the calibration curve can be formed without using the calibrating wafer, such an inconvenience can be solved. Such a function and its operation will be described in detail hereinbelow.

The surface inspecting apparatus of the embodiment has calibration curve forming software. This software has storage areas such as reference light intensity database, calibrating wafer data, standard particle data table, standard particle counter, and data table to form the calibration curve.

Figure 8A:
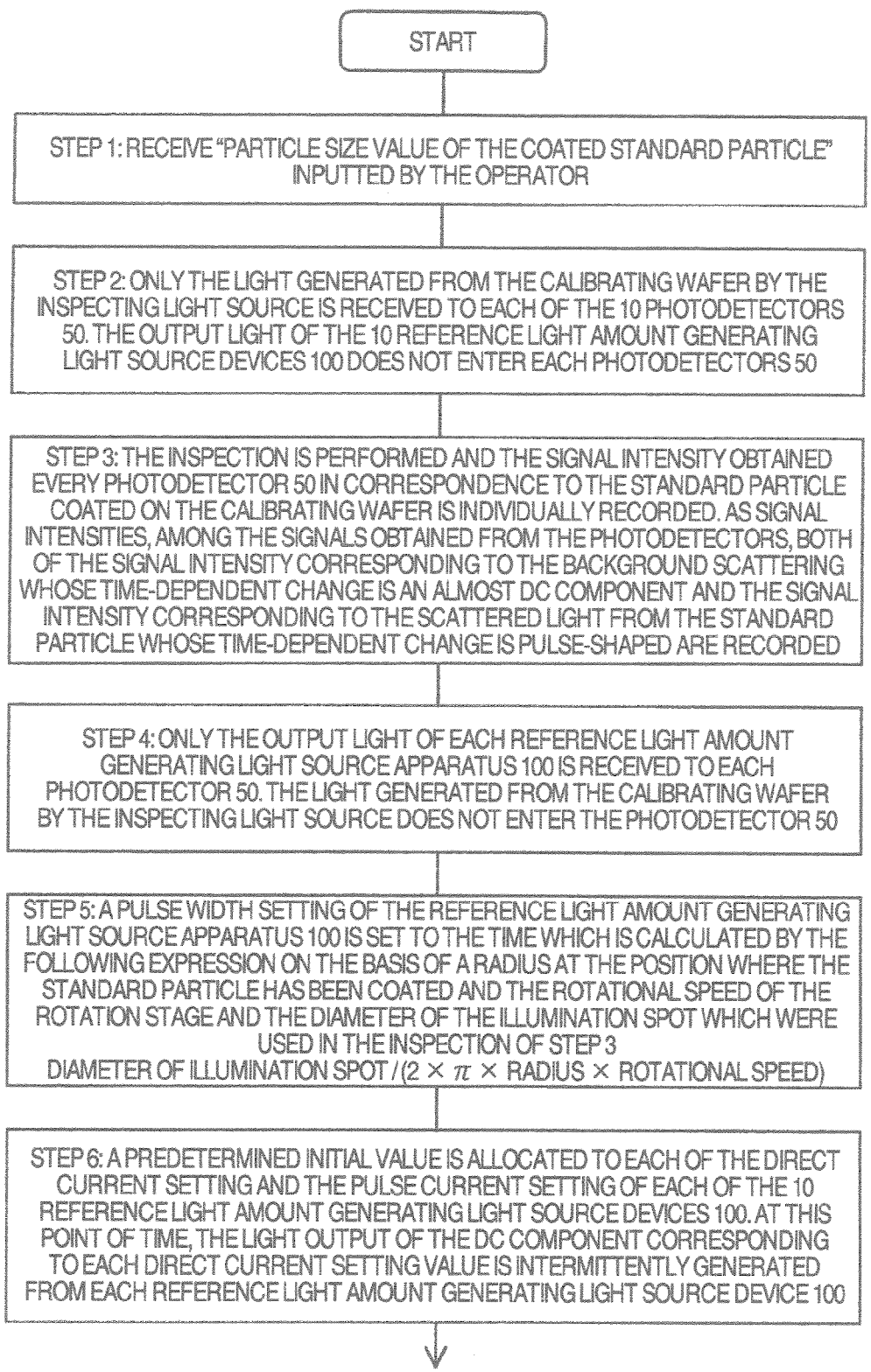
FIG. 8(a) is a flowchart showing a flow for forming a reference light intensity database in the embodiment 1.
Figure 8B:
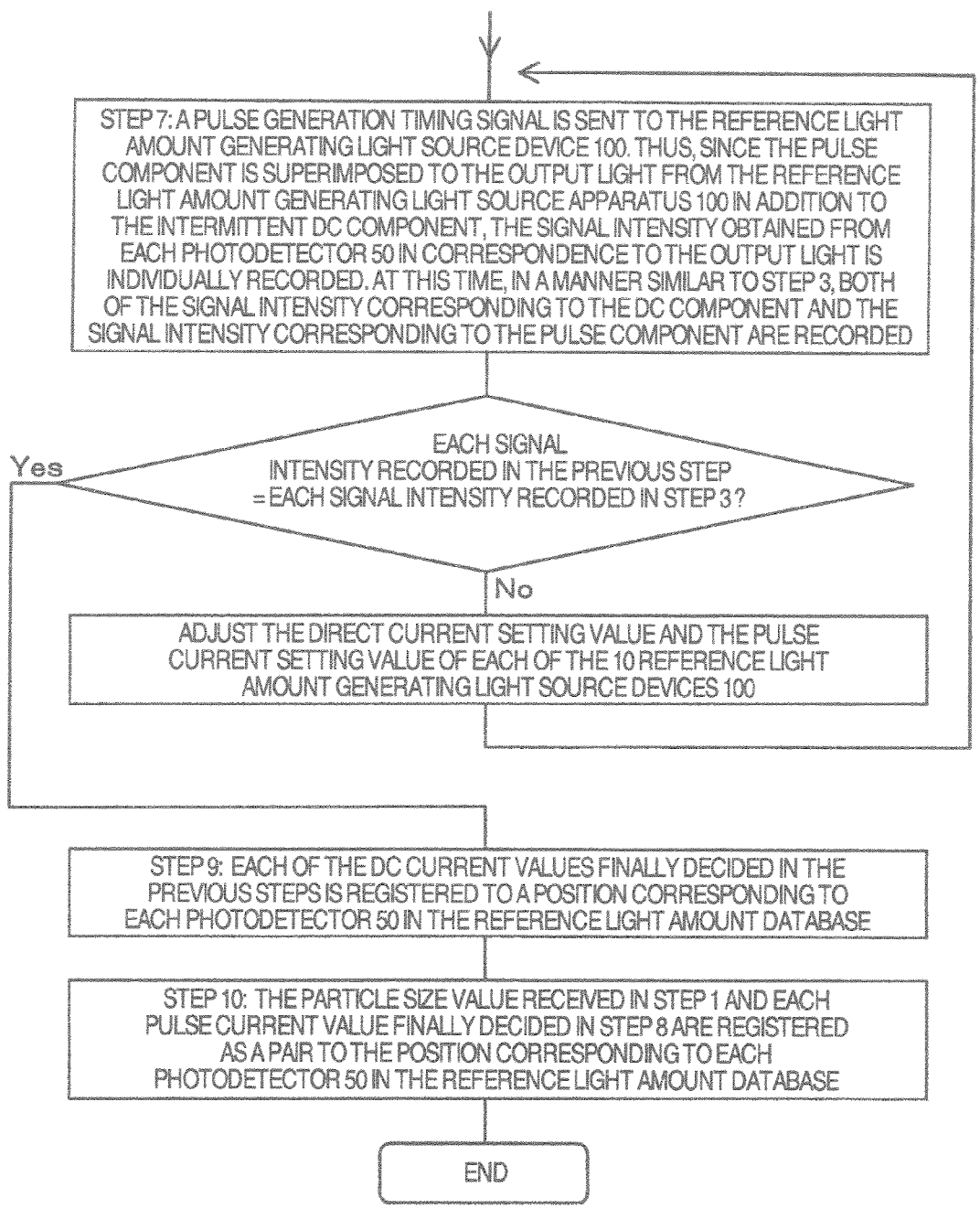
FIG. 8(b) is a flowchart showing the flow for forming the reference light intensity database in the embodiment 1.

First, by executing the following processes, the surface inspecting apparatus of the embodiment forms the reference light intensity database in which parameter values necessary for allowing the reference light intensity generating light source device to generate a desired amount of light have been stored. FIG. 8 shows a flowchart showing a flow for forming the reference light intensity database.

Prior to executing the following processes, the operator prepares a calibrating wafer which has a surface state (film formation, surface roughness, and the like) similar to that of the semiconductor wafer as an inspection target and which is obtained by adhering a circumference of a predetermined radius (for example, 75 mm) of a clean semiconductor wafer with standard particles (generally, PSL: polystyrene latex spheres are used) having particle sizes adapted to register data into the reference light intensity database, it is assumed that after inspection conditions (including a diameter and an illuminance of the illumination spot for illuminating the calibrating wafer) of the surface inspecting apparatus of the embodiment were set in accordance with inspection conditions of the inspection which is executed to the actual inspection target wafer, the inspection of the calibrating wafer is started.

Step 1: "A particle size value of the adhered standard particle" which was inputted by the operator is received.

Step 2: It is constructed in such a manner that only the light which is generated from the calibrating wafer by the light from the light source for inspection is received to each of the ten photodetectors 50 and the output light of the ten reference light intensity generating light source devices 100 does not enter each photodetector 50.

Step 3: The inspection is executed and the signal intensity obtained every photodetector 50 is individually recorded in correspondence to the standard particle adheres to the calibrating wafer. As a signal intensity, among the signals which are obtained from the photodetectors, both of the signal intensity corresponding to the background scattering in which the time-dependent change is an almost DC component and the signal intensity corresponding to the scattered light from the standard particle in which the time-dependent change is a pulse-shaped are recorded.

Step 4: Subsequently, it is constructed in such a manner that only the output light of each reference light intensity generating light source device 100 is received to each photodetector 50 and the light which is generated from the calibrating wafer by the light from the light source for inspection does not enter the photodetectors 50.

Step 5: The pulse width setting of the reference light intensity generating light source device 100 is set to a time which is calculated by the following expression on the basis of a radius at the position where the standard particle has been adhered and a rotational speed of the rotation stage and the diameter of the illumination spot which were used in the inspection of Step 3.

Diameter of the Illumination Spot/($2\times\pi\times$Radius$\times$Rotational Speed)

Step 6: A predetermined initial value is allocated to each of the direct current setting and the pulse current setting of each of the ten reference light intensity generating light source devices 100. At this point of time, a ht output of the DC component corresponding to each of the DC setting values is continuously generated from each reference light intensity generating light source device 100.

Step 7: A pulse generation timing signal is supplied to the reference light intensity generating light source device 100. Thus, the pulse component is superimposed to the output light from the reference light intensity generating light source device 100 in addition to the foregoing continuous DC component. Therefore, the signal intensities which are obtained from the photodetectors 50 are individually recorded in correspondence to the output light. At this time, both of the signal intensity corresponding to the DC component and the signal intensity corresponding to the pulse component are recorded in a manner similar to Step 3.

Step 8: Until each signal intensity recorded in Step 7 is equal to each signal intensity recorded in Step 3, the direct current setting value and the pulse current setting value of each of the ten reference light intensity generating light source devices are adjusted and Step 7 is repeated.

Step 9: Each of the direct current current values (DC current values) which were finally decided in Step 8 is registered to the position corresponding to each photodetector 50 in the reference light intensity database.

Step 10: The particle size value received in Step 1 and each pulse current value which was finally decided in Step 8 are registered as a pair to the position corresponding to each photodetector 50 in the reference light intensity database.

If there are a plurality of particle sizes whose data should be registered into the reference light intensity database, it is sufficient to repeat the foregoing operations the necessary number of times from the preparation of the calibrating wafer.

Figure 9:
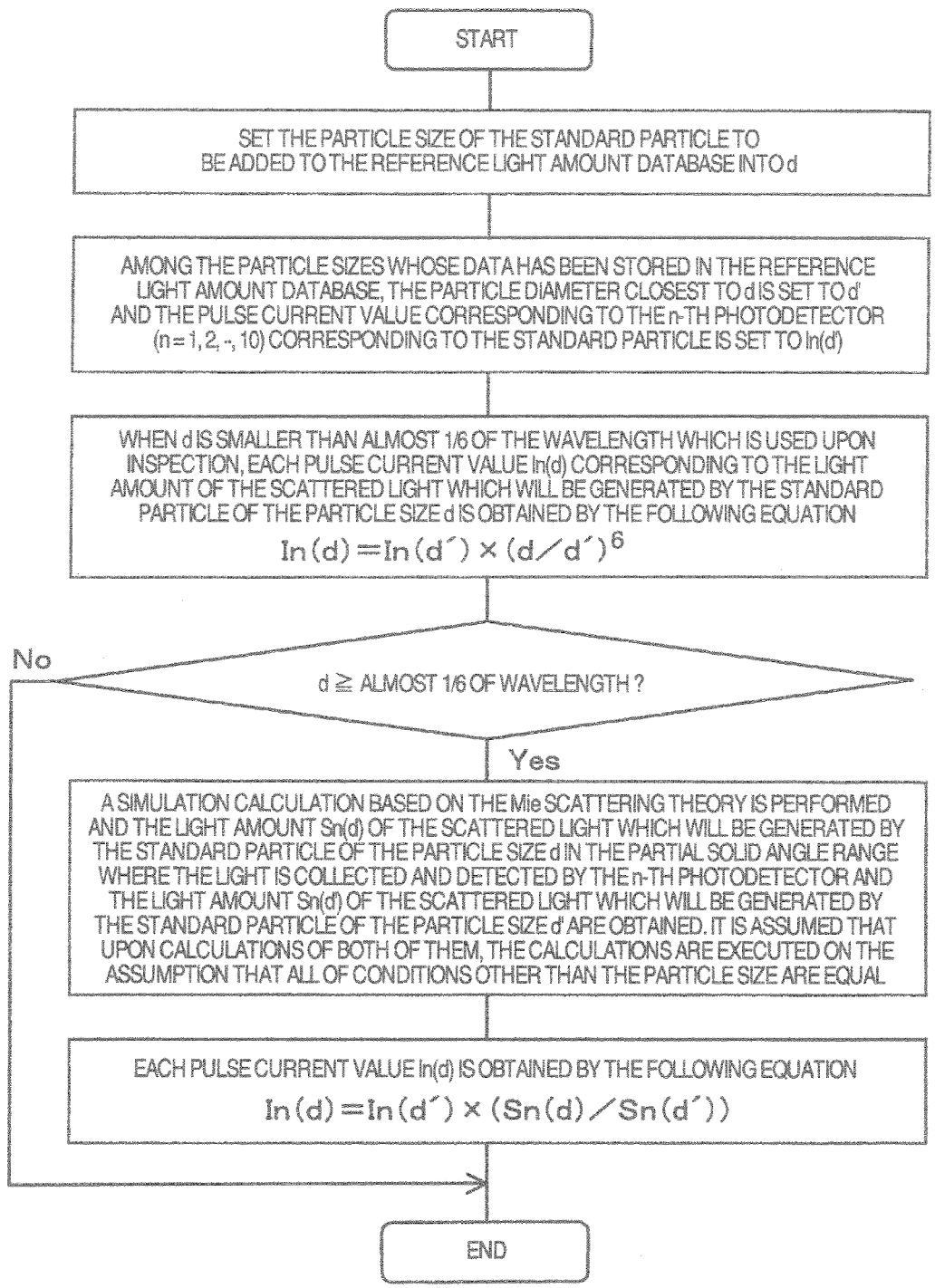
FIG. 9 is a flowchart showing a flow for a process for adding data corresponding to a particle size which does not exist in a particle size series of a standard particle in the embodiment 1.

Also with respect to a particle size of a value which does not exist in a particle size series of the standard particles, when assuming that the standard particle of such a particle size existed, each pulse current value $In(d)$ corresponding to a light intensity of scattered light which will be generated by such a standard particle is calculated and obtained by the following procedure and can be added to the reference light intensity database. FIG. 9 shows a flowchart showing a flow of a process for adding data corresponding to the particle size which does not exist in the particle size series of the standard particles.

Step 1: A particle size of the standard particle to be added to the reference light intensity database is assumed to be d.

Step 2: In order to precisely obtain $In(d)$, a particle size which is closest to d among the particle sizes whose data has been stored in the reference light intensity database is assumed to be d'. A pulse current value corresponding to the nth photodetector (n=1, 2, . . . , 10) corresponding to such a standard particle is assumed to be $In(d')$.

Step 3: When d is smaller than almost ⅙ of the wavelength which is used upon inspection, the particle size d lies within the Rayleigh scattering region. In the Rayleigh scattering region, since the light intensity of the light which is scattered by the defect is proportional to the particle size to the power of six, each pulse current value $In(d)$ corresponding to the light intensity of the scattered light which will be generated by such a standard particle of the particle size d is obtained by the following equation.

$$In(d)=In(d')\times(d/d')^6$$

Step 4: When d is larger than the discrimination reference of Step 3, since the particle size d lies within the Mie scattering region, each pulse current value $In(d)$ corresponding to the light intensity of the scattered light which will be generated by the standard particle of the particle size d due to processes of Step 5 and subsequent steps is obtained.

Step 5: A simulation calculation based on a Mie scattering theory is executed. A light intensity $Sn(d)$ of the scattered light which will be generated by the standard particle of the particle size d in a small solid angle range where the light is collected and detected in the n-th photodetector and a light intensity $Sn(d')$ of the scattered light which will be generated by the standard particle of the particle size d' in such a range are obtained. It is assumed that all conditions other than the particle size upon calculation of both of the light intensities are equal and they are calculated.

Step 6: Each pulse current value $In(d)$ is obtained by the following equation.

$$In(d)=In(d')\times(Sn(d)/Sn(d'))$$

Or, if a transmission efficiency ηn of each collection optics existing on an optical path starting from the illumination spot on the inspection wafer and reaching each of the photodetectors has previously been known, a pulse current of the light source device at the time when the light intensity obtained by multiplying $Sn(d)$ by ηn, that is, ηn×$Sn(d)$ can be derived from the light source device may be used as $In(d)$.

Subsequently, by executing processes shown in a flowchart of FIG. 10, the surface inspecting apparatus of the embodiment can form the calibration curve by using the reference light intensity generating light source device 100. When the calibration curve is formed, it is assumed that the operator preliminarily inputs a parameter group shown in FIG. 11 to the surface inspecting apparatus through a GUI or the like.

It is also assumed that in correspondence to those inputted parameter group, (1) each DC current value necessary for allowing each of the reference light intensity generating light source devices 100 to generate the light intensity corresponding to the intensity of the light which is collected and detected in each photodetector 50 in the background scattering generated by the calibrating wafer has previously been stored in the calibrating wafer data.

(2) The particle size of the standard particle and (3) data pairs of each pulse current value necessary for allowing each of the reference light intensity generating light source devices 100 to generate the light intensity corresponding to the intensity of the light which is collected and detected in each photodetector 50 in the scattered light generated by the standard particle of the particle size of (2)

have previously been stored in the standard particle data table by the number of kinds of particle sizes necessary to form the calibration curve.

It is now assumed that each numerical value of (1), (2), and (3) is obtained by referring to data in the standard particle data table which has previously been formed as mentioned above.

Step 1: Parameters regarding the output signal of each photodetector 50 such as applied voltage of the photomultiplier tube of each photodetector 50, gain of a signal amplifier, and the like are set to proper values in accordance with the inspection conditions to which the calibration curve to be formed has been made to correspond in a manner such that the output signal is not saturated and the sufficient output signal can be obtained.

Step 2: It is constructed in such a manner that only the output light of each reference light intensity generating light source device 100 is received to each photodetector 50 and the light generated from the calibrating wafer by the inspecting light source does not enter the photodetector 50.

Step 3: A pulse width setting of each reference light intensity generating light source device 100 is set to a time which is calculated by the following expression on the basis of the rotational speed of the rotation stage and the diameter of the illumination spot which are used under the inspection conditions to which the calibration curve to be formed has been made to correspond and a value of the radius at the position where the standard particle is adhered upon formation of the calibrating wafer.

Diameter of the Illumination Spot/(2×π×Radius×Rotational Speed)

Step 4: The DC current value corresponding to each photodetector 50 stored in the calibrating wafer data is read out.

Step 5: A value of a standard particle counter (hereinbelow, referred to as M) is set to 1.

Step 6: The particle size value, the DC current value corresponding to each photodetector 50, and the pulse current value which have been stored as an M-th data set in the standard particle data table are read out.

Step 7: The DC current value read out in Step 4 and the pulse current value read out in Step 6 are set into each reference light intensity generating light source device 100, thereby allowing the light corresponding to those values to be generated.

Step 8: The light emitted in Step 7 is detected by each photodetector 50 and each signal intensity value (both of the signal intensity corresponding to the DC component and the signal intensity corresponding to the pulse component) which is obtained at that time and the particle size value read out in Step 6 are individually stored as an M-th data set in the calibration curve forming data table every photodetector 50.

Step 9: Until the processes are finished with respect to all data in the standard particle data table, the processes of Step 6 to Step 8 are repeated while increasing a value of M one by one.

Step 10: The calibration curve is formed by executing a statistical arithmetic operation such as a method of least squares or the like from the data set stored in the calibration curve forming data table.

As mentioned above, in the surface inspecting apparatus of the embodiment, the calibration curve can be formed without using the calibrating wafer.

In a plurality of reference light intensity generating light source devices, the light intensities of the output light are detected by an light power which can preliminarily measure an absolute value of the light intensity by using W (watt), the number of photons per unit time, or their derived unit system, and if each light source device is adjusted in such a manner that the output light of the same intensity is extracted from all of the plurality of light source devices under conditions in which the setting value of the direct current, the setting value of the pulse current, and the setting value of the pulse width are respectively equal to predetermined values, the calibration curves are formed under the same conditions in a plurality of surface inspecting apparatuses in each of which the light source device has been built. Therefore, naturally, the apparatuses act advantageously so as to suppress differences among the sensitivity characteristics of the apparatuses.

Further, as another effect, since a magnitude of the output signal of each photodetector can be converted into W (watt) or the number of photons per unit time or their derived unit system, the intensity of the scattered light which is generated from the inspection object can be displayed by the absolute value of the light intensity.

The reference light intensity generating light source device 100 in the embodiment can be applied to various inspecting apparatuses other than that in the embodiment if it can input the light from the reference light intensity generating light source device to the photodetector.

For example, if the optical fiber 20 for emitting the light froze the reference light intensity generating light source device is constructed in an array shape, the light from the reference light intensity generating light source device can be inputted to each pixel of the CCD array or a TDI.

At this time t is not always necessary that the number of array-shaped optical fibers 20 and the number of pixels of the CCD array or TDI coincide.

FIG. 12 shows an example of a case where light 240 from the reference light intensity generating light source device is inputted to a one-dimensional CCD 250 by using the array-shaped optical fibers 20.

[Embodiment 2]

An embodiment 2 will be subsequently described.

In the embodiment 2, the output signal at the time when the light from the light source device in FIG. 1 has entered the photodetector 50 is observed by an oscilloscope or the like, so that a discrimination that the photodetector 50 to be built in the surface inspecting apparatus is good or not can be made prior to assembling the surface inspecting apparatus.

At this time, as mentioned above, values corresponding to the actual inspection conditions using the surface inspecting apparatus are set into (1) a setting value to the direct current setting value input unit 6, (2) a setting value to the pulse current setting value input unit 7 and a switching of the ND filter 12, (3) a setting value to the pulse width input unit 8, and (4) a setting value to the pulse repetition interval input unit 9 of the present light source device as mentioned above. When the output signal of the photodetector 50 is observed, an amplification or a frequency filtering is properly performed if necessary. By those operations, the photodetector 50 can be evaluated good or not for the light input which simulated a state at the time when the surface inspecting apparatus has actually been operated.

By using the present light source device, as test items of the discrimination that the photodetector is good or not, the following items regarding the puke light emission can be included:

1. response linearity to the pulse light emission (showing such characteristics that when the intensity of the pulse light emission has been increased at a predetermined rate, whether or not the output increases by an amount corresponding to it), and 2. saturation characteristics to the pulse light emission (showing such characteristics that whether or not a saturation occurs to which extent the intensity of the pulse light emission becomes).

The present light source device is constructed by parts of the number which is smaller than that of the general surface inspecting apparatus and can be manufactured at reasonable costs. Therefore, it is suitable for manufacturing a plurality of apparatuses.

However, "even if the setting values to the direct current setting value input units 6 and the setting values to the pulse current setting value input units 7 in the plurality of manufactured light source devices are respectively equalized, there is a difference between the light intensities which are outputted from the optical fibers 20", there is such a possibility that "if the photodetector is evaluated by using the different light source devices, different discrimination results are obtained".

In the present light source device of the embodiment, in order to avoid such a possibility, the light intensity which is extracted from the outgoing side end surface of the optical fiber 20 when the present light source device is operated by setting the setting value to the direct current setting value input unit 6, the setting value to the pulse current setting value input unit 7, and the setting value to the pulse width input unit 8 into the predetermined conditions is detected by the light power which can preliminarily measure the absolute value of the light intensity by using W (watt), the number of photons per unit time, or their derived unit system, and the amplification factors of the direct current amplifier 21 and the pulse current amplifier 31 are adjusted in such a manner that the output light of the same intensity is extracted from all of the plurality of light source devices under the conditions in which the setting value to the direct current setting value input unit 6, the setting value to the pulse current setting value input unit 7, and the setting value to the pulse width input unit 8 are set into the predetermined values. By this procedure, even in the case of using the plurality of light source devices, such a possibility that "if the photodetector is evaluated by using the different light source devices, different discrimination results are obtained" can be suppressed.

In the light source device of the embodiment, in the surface inspecting apparatus serving as a target to be simulated, it is constructed so as to generate the light signal which simulated the wavelength, the light intensity, and the time-dependent change of the light intensity of the light which is scattered, diffracted, or reflected by the surface of the inspection object and enters the photodetector. However, for example, in the case where the sensitivity of the photodetector 50 to be evaluated has a polarization dependency, in addition to each of the above items, it is desirable to generate the light signal which also simulated a feature of a polarizing state.

REFERENCE SIGNS LIST

1 Light emitting element
2 Direct current generating unit
3 Pulse current generating unit
4 Current adder
6 Direct current setting value input unit
7 Pulse current setting value input unit
8 Pulse width input unit
9 Pulse repetition interval input unit
10 Condenser lens
11 Beam splitter
12 ND filter
13 Switching mechanism
14 Light intensity monitoring detector
20 Optical fiber
21 Direct current amplifier
31 Pulse current amplifier
40 Microcomputer for control
41 Control interface of light source device for generating reference light intensity
50 Photodetector
61 Direct current setting interface
71 Pulse current setting interface
81 Pulse width setting interface
91 Pulse generation timing signal interface
100 Light source device for generating reference light intensity
101 Defect
111 Light source
126 Amplifier
130 A/D converter
140 Sampling control unit
150 Sampling data averaging unit
200 Semiconductor wafer
201 Chuck
202 Inspection object moving stage
203 Rotation stage
204 Translation stage
205 Z stage
206 Inspection coordinates detecting unit
208 Defect discriminating unit
210 Illumination optics and Detection optics
220 Particle size calculating unit
230 Defect coordinates detecting unit
240 Light from reference light intensity generating apparatus
250 One-dimensional CCD

The invention claimed is:

1. An inspecting apparatus comprising:
a first illumination system configured to supply a sample to be inspected with light;
a detection system configured to detect light from the sample to be inspected;
a second illumination system configured to supply the detection system with simulated light, and configured to not supply simulated light to the sample,
wherein the simulated light defines a time property of light from a standard sample of a predetermined size; and
a processing system configured to acquire a function for translating a detection result of the detection system by illumination of the first illumination system into a size of a defect on the basis of a detection result in which the detection system detects the simulated light.

2. The system according to claim 1,
wherein the simulated light includes a pulse component configured to correspond to the predetermined size of the standard sample.

3. The system according to claim 2,
wherein the simulated light includes light in a Rayleigh scattering region.

4. The system according to claim 3,
wherein the simulated light includes light from the Rayleigh scattering region to a Mie scattering region.

5. The system according to claim 4,
wherein the simulated light includes a continuous component configured to correspond to a surface condition of sample to be inspected.

6. The system according to claim 5, further comprising:
an emitter configured for generating the simulated light;
a pulse current supplying system configured for supplying the emitter with pulse current;
a continuous current supplying system configured for supplying the emitter with continuous current; and
a detector configured to detect a part of the light from the emitter,
wherein at least one of the pulse current supplying system and the continuous current supplying system is configured to supply the emitter with at least one of the pulse current and the continuous current so as that detection result of the detector is substantially constant.

7. The system according to claim 6, further comprising:
a movable dimmer arranged in optical path of the simulated light.

8. The system according to claim 7, further comprising:
a processing system configured to acquire a function for translating a detection result of the detection system into a size of a defect on the basis of a detection result that the detection system detects the simulated light.

9. The system according to claim 1,
wherein the simulated light includes light in a Rayleigh scattering region.

10. The system according to claim 9,
wherein the simulated light includes light from the Rayleigh scattering region to a Mie scattering region.

11. The system according to claim 1,
wherein the simulated light includes a continuous component configured to correspond to a surface condition of the sample.

12. The system according to claim 1, further comprising:
an emitter configured to generate the simulated light;
a pulse current supplying system configured to supply the emitter with pulse current;
a continuous current supplying system configured to supply the emitter with continuous current;
a detector configured to detect a part of the light from the emitter,
wherein at least one of the pulse current supplying system and the continuous current supplying system is configured to supply the emitter with at least one of the pulse current and the continuous current so as that detection result of the detector is substantially constant.

13. The system according to claim 1, further comprising:
a movable dimmer arranged in optical path of the simulated light.

14. The system according to claim 1, further comprising:
a processing system configured to acquire a function for translating a detection result of the detection system into a size of a defect on the basis of a detection result that the detection system detects the simulated light.

15. An inspecting apparatus comprising:
a first illumination system configured to supply a sample to be inspected with light;
a detection system configured to detect light from the sample to be inspected;
a second illumination system configured to supply the detection system with simulated light of a sample, and configured to not supply simulated light to the sample,
wherein the simulated light defines a time property of light from a standard sample of a predetermined size; and
a processing system configured to acquire a function for translating a detection result of the detection system by illumination of the first illumination system into a size of a defect on the basis of a detection result in which the detection system detects the simulated light.

16. The inspection apparatus according to claim 15, wherein the simulated light includes a pulse component configured to correspond to the predetermined size of the standard sample.

17. The inspection apparatus according to claim 16, wherein the simulated light includes light in a Rayleigh scattering region.

18. The inspection apparatus according to claim 17, wherein the simulated light includes light from the Rayleigh scattering region to Mie scattering region.

19. The inspection apparatus according to claim 18, wherein the simulated light includes a continuous component corresponding to a surface condition of the sample to be inspected.

20. The inspection apparatus according to claim 19, wherein the second illumination system includes:
an emitter configured to generate the simulated light;
a pulse current supplying system configured to supply the emitter with a pulse current;
a continuous current supplying system configured to supply the emitter with a continuous current;
a detector configured to detect a part of the simulated light from the emitter,
wherein at least one of the pulse current supplying system and the continuous current supplying system supplies the emitter with at least one of the pulse current and the continuous current so as that a detection result of the detector is substantially constant.

21. The inspection apparatus according to claim 20, wherein the second illumination system includes a movable dimmer which is arranged in an optical path of the second illumination system.

22. The inspection apparatus according to claim 15, wherein the simulated light includes light in the Rayleigh scattering region.

23. The inspection apparatus according to claim 22, wherein the simulated light includes light from the Rayleigh scattering region to a Mie scattering region.

24. The inspection apparatus according to claim 15, wherein the simulated light includes a continuous component corresponding to a surface condition of the sample to be inspected.

25. The inspection apparatus according to claim 15, wherein the second illumination system includes:
an emitter configured to generate the light;
a pulse current supplying system configured to supply the emitter with a pulse current;
a continuous current supplying system configured to supply the emitter with a continuous current;
a detector configured to detect a part of the light from the emitter,
wherein at least one of the pulse current supplying system and the continuous current supplying system supplies the emitter with at least one of the pulse current and the continuous current so as that a detection result of the detector is substantially constant.

26. The inspection apparatus according to claim 25, wherein the second illumination system includes a movable dimmer which is arranged in an optical path of the second illumination system.

27. A method for adjusting an inspecting apparatus comprising:
supplying a sample to be inspected with light from a first illumination system;
detecting light from the sample to be inspected with a detection system;
supplying the detection system with simulated light with a second illumination system, wherein the simulated light is not supplied to the sample,
wherein the simulated light defines a time property of light from a standard sample which has a predetermined size; and
acquiring a function for translating a detection result of the detection system by illumination of the first illumination system into a size of a defect on the basis of a detection result in which the detection system detects the simulated light with a processing system.

28. The method according to claim 27, wherein the simulated light includes a pulse component configured to correspond to the predetermined size of the standard sample.

29. The method according to claim 28, wherein the simulated light includes light in a Rayleigh scattering region.

30. The method according to claim 29, wherein the simulated light includes light from the Rayleigh scattering region to a Mie scattering region.

31. The method according to claim 30, wherein the simulated light includes a continuous component configured to correspond to a surface condition of the sample to be inspected.

32. The method according to claim 31, further including the steps of:
generating the simulated light with an emitter which is part of the second illumination system,
supplying the emitter with a pulse current with a pulse current supplying system, supplying the emitter with a continuous current with a continuous current supplying system, detecting a part of the simulated light from the emitter with a detector, and supplying the emitter with at least one of the pulse current and the continuous current so as that a detection result of the detector is substantially constant.

33. The method according to claim 32, wherein the second illumination system includes a movable dimmer which is arranged in an optical path of the second illumination system.

34. The method according to claim 27, wherein the simulated light includes light in the Rayleigh scattering region.

35. The method according to claim 34, wherein the simulated light includes light from the Rayleigh scattering region to a Mie scattering region.

36. The method according to claim 27, wherein the simulated light includes a continuous component corresponding to a surface condition of sample to be inspected.

37. The method according to claim 27, further including the steps of:

generating the simulated light with an emitter which is part of the second illumination system, supplying the emitter with a pulse current with a pulse current supplying system, supplying the emitter with a continuous current with a continuous current supplying system, detecting a part of the simulated light from the emitter with a detector, and supplying the emitter with at least one of the pulse current and the continuous current so as that a detection result of the detector is substantially constant.

38. The method according to claim 37, wherein the second illumination system includes a movable dimmer arranged in an optical path of the second illumination system.

* * * * *